United States Patent [19]

Kawamura et al.

[11] Patent Number: 4,767,886
[45] Date of Patent: Aug. 30, 1988

[54] METHOD FOR PREPARING LOWER OLEFINS

[75] Inventors: Kichinari Kawamura; Yasuo Kono; Hideo Okado; Hiroyuki Hagiwara; Haruo Takaya, all of Ibaraki, Japan

[73] Assignee: Director-General of Agency of Industrial Science and Technology, Tokyo, Japan

[21] Appl. No.: 22,222

[22] Filed: Mar. 5, 1987

[30] Foreign Application Priority Data

Mar. 6, 1986 [JP] Japan ................................. 61-49367

[51] Int. Cl.$^4$ ............................................... C07C 1/00
[52] U.S. Cl. ................................................. 585/640
[58] Field of Search ......................................... 585/640

[56] References Cited

U.S. PATENT DOCUMENTS

| 4,066,714 | 1/1978 | Rodewald | 585/640 |
| 4,292,458 | 9/1981 | Klotz | 585/640 |
| 4,544,793 | 10/1985 | Okado et al. | 585/640 |

FOREIGN PATENT DOCUMENTS

| 0071437 | 2/1983 | European Pat. Off. | 585/640 |
| 0114498 | 8/1984 | European Pat. Off. | 585/640 |
| 3524890 | 1/1986 | Fed. Rep. of Germany | 585/640 |

Primary Examiner—Curtis R. Davis
Attorney, Agent, or Firm—Birch, Stewart, Kolasch & Birch

[57] ABSTRACT

Here is disclosed a method for preparing lower olefins by bringing methanol and/or dimethyl ether into contact with a catalyst in a gaseous phase. In this method, the contact between the methanol and/or dimethyl ether and the catalyst is carried out at a weight hourly space velocity of 0.1 to 20 hr$^{-1}$ at a reaction temperature of 300° to 650° C. under a total pressure of 0.1 to 100 atm by the use of, as the catalyst, an alkaline earth metal-modified alkaline earth metal-containing zeolite catalyst; the alkaline earth metal-modified alkaline earth metal-containing zeolite catalyst being prepared as disclosed in the Specification by modifying an alkaline earth metal-containing aluminoborosilicate so that the alkaline earth metal in an amount of at least 0.25% by weight in terms of the metal may be mixed with or supported in the zeolite catalyst.

9 Claims, 1 Drawing Sheet

METHOD FOR PREPARING LOWER OLEFINS

BACKGROUND OF THE INVENTION

1. Field of the Invention

The present invention relates to a method for preparing lower olefins from methanol and/or dimethyl ether, and more specifically it relates to a method for preparing lower olefins such as ethylene and propylene from methanol and/or dimethyl ether by the use of catalyst with a high selectivity and is stable for a long term, the used catalyst being an alkaline earth metal-containing aluminoborosilicate modified with an alkaline earth metal compound.

2. Description of the Prior Art

In recent years, the supply of crude oil is unstable, and particularly in countries which depend largely on foreign countries for the oil, an effective utilization of coals and natural gases is taken up as an important theme. It is now desired to establish an industrially synthetic method of preparing organic compounds such as olefins, paraffins and aromatic compounds by using, as a raw material, methanol which can be obtained from methane, CO and the like.

Nowadays, low-cost ethylene has been produced from natural gases, and it can be presumed that ethylene and ethylene derivatives will be manufactured excessively in the near future. As a result, if the manufacture of the ethylene is controlled, the manufacture of propylene which is produced together with the ethylene will also be curtailed, and in consequence, the shortage of propylene in the future can be supposed. For this reason, it is sought to develop a method for manufacturing lower olefins such as ethylene and propylene simultaneously and stable in high yield.

It is known in the art that silica, alumina, crystalline aluminosilicate and the like have been heretofore employed as catalysts for hydrocarbon conversion. The crystalline aluminosilicate contains pores or tunnels therein having a certain diameter, depending on its kind, and therefore it has the shape selectivity that molecules alone which satisfy specific conditions are selectively adsorbed out of various molecules which are mixed. Accordingly, such a crystalline aluminosilicate is also called a molecular sieve generally.

In the 1970's, Mobil Oil Co., Ltd. has developed a ZSM-5 type zeolite catalyst as the shape selectivity catalyst which can manufacture hydrocarbons containing high-quality gasolines as the main components from methanol or dimethyl ether. This zeolite is different from conventional ones, because it permits freely controlling a molar ratio of $SiO_2/Al_2O_3$ and has an excellent property such as a remarkably high heat resistance. By utilizing the features of the new zeolite, it is possible to prepare a product containing lower olefins as main components through a conversion reaction of methanol and/or dimethyl ether. For example, according to the specification of West German Pat. No. 2935863, it is known that the active type zeolite (H-ZSM-5) of $SiO_2/Al_2O_3 = 35$ to 1600 (molar ratio) can produce lower olefins (carbon number = 2 to 4) in a maximum yield of 70.1% by weight in a methanol conversion reaction within a temperature range of 350° to 600° C. It is described in examples of the West German Patent that an optimum composition of the ZSM-5 type zeolite and the reaction temperature are $SiO_2/Al_2O_3 = 298$ to 500 (molar ratio) and 550° C., respectively. Accordingly, in order to form a hydrocarbon containing the lower olefins as main components from methanol and/or dimethyl ether, it is definitely advantageous that the reaction temperature is as high as possible, but the methanol conversion reaction at such a high temperature as about 550° C. will often lead to a rapid deterioration in the catalyst, for example, even the ZSM-5 type zeolite catalyst having a high heat resistance. Thus, for the purpose of manufacturing the lower olefins at a temperature of 500° C. or more from a raw material such as methanol and/or dimethyl ether in a high yield for a long term without involving a rapid decline in the catalyst, it is necessary to develop a novel zeolite by which benzene, toluene and xylene (B. T. X.) which can be supposed as coke precursors are less produced and which does not bring about an activity decline easily at a high temperature of 550° C. or more.

From such a viewpoint, the inventors of the present application have intensively researched to develop a catalyst which scarcely deteriorates in the conversion reaction of methanol and/or dimethyl ether at a high temperature of 500° C. or more at which the production of the lower olefins is advantageous, and as a result, it has been found that a finely crystalline alkaline earth metal-containing aluminoborosilicate (hereinafter referred to simply as aluminoborosilicate on occasion) which has been synthesized by adding boron and a salt of an alkaline earth metal at the time of its synthesis is suitable for this object, is remarkably excellent in selectivity of the lower olefins, and provides a less production of B. T. X. This fact has been already disclosed (Japanese Patent Application No. 245435/1985). However, even in the case of this catalyst, its activity deteriorates owing to the deposition of carbon onto the catalyst, as reaction time elapses, and thus it cannot withstand long-term use sufficiently.

The present inventors have continued the research with the intention of prolonging the life of the catalyst, and in the end, they have found that when the above mentioned alkaline earth metal-containing aluminoborosilicate is further modified with an alkaline earth metal compound such as a salt, an oxide or a hydroxide of an alkaline earth metal, an extremely noticeable improvement is made unexpectedly. The present invention has been completed on the basis of this finding.

SUMMARY OF THE INVENTION

The present invention is directed to a method for preparing lower olefins, characterized by bringing methanol and/or dimethyl ether into contact with a catalyst in a gaseous phase, the catalyst being an alkaline earth metal-modified alkaline earth metal-containing zeolite catalyst in which an alkaline earth metal for the modification is mixed or supported in an amount of at least 0.25% by weight in terms of the metal, the alkaline earth metal-containing zeolite catalyst being prepared by first subjecting, to a hydrothermal treatment at a temperature of 80° to 250° C., a material which satisfies composition conditions of an $SiO_2/Al_2O_3$ molar ratio = 12 to 3,000, an $SiO_2/B_2O_3$ molar ratio = 1 to 1,000, an $OH^-/SiO_2$ molar ratio = 0.02 to 10, an $H_2O/SiO_2$ molar ratio = 1 to 2,000, a tetrapropylammonium compound/$SiO_2$ molar ratio = 0.01 to 3 and an alkaline earth metal/Al gram-atom ratio (hereinafter referred to as atomic ratio) = 0.03 to 300 in order to form an alkaline earth metal-containing aluminoborosilicate having a composition of $$aM^1_2O \cdot bM^2O \cdot Al_2O_3 \cdot B_2O_3 \cdot cSiO_2 \cdot nH_2O$$

wherein $M^1$ is an alkali metal and/or a hydrogen atom, $M^2$ is an alkaline earth metal, a is a value of 0 to 2, b is a value of 0.1 to 100, c is a value of 12 to 3,000 and n is a value of 0 to 30; and then modifying the alkaline earth metal-containing aluminoborosilicate with an alkaline earth metal compound in solid or solution circumstances.

Therefore, an object of the present invention is to provide a method for preparing lower olefins from methanol and/or dimethyl ether, and according to this method, the raw material is less decomposed into CO and $CO_2$, the lower olefins can be prepared in high selectivity, paraffins and aromatic hydrocarbons are less formed secondarily, the deposition of carbon onto the catalyst can be inhibited, and the deterioration in catalyst activity can be prevented even at a high temperature.

Another object of the present invention is to provide a method for preparing lower olefins from methanol and/or dimethyl ether at a temperature as high as 500° C. or more in a high yield in the presence of a certain catalyst containing an alkaline earth metal.

Still another object of the present invention is to provide a catalyst which is suitable for the manufacture of ethylene and propylene from methanol and/or dimethyl ether in high yield.

Other and further objects, features and advantages of the invention will appear more fully from the following description.

DETAILED DESCRIPTION OF THE INVENTION

Figure 1:
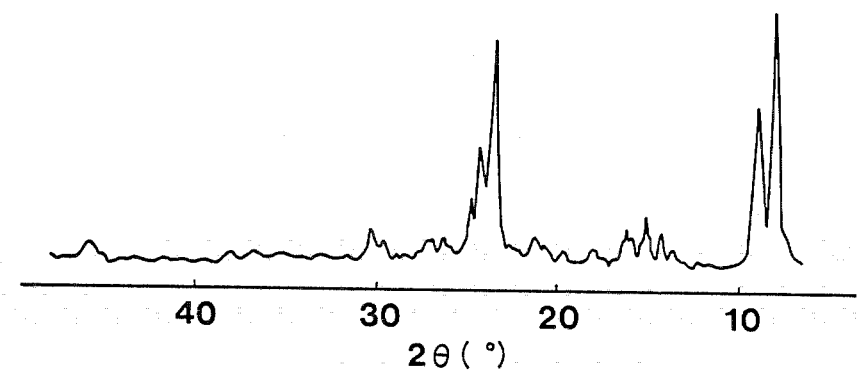
FIG. 1 is an X-ray deffraction pattern of calcium-containing aluminoborosilicate obtained in Preparation 1 of the present invention.

In the present invention, lower olefins means olefins the number of carbon atoms of which is within the range of 2 to 4, including ethylene, propylene, butene, etc.

An alkaline earth metal-containing aluminoborosilicate which is a raw material of a catalyst used in a method of the present invention is a fine crystal having a novel structure, and can be manufactured by a variety of methods, but that which has been manufactured by the following method is preferable.

That is, in addition to a silica source, an alumina source and an alkali metal source which are used in manufacturing a usual zeolite, a boron source and an alkaline earth metal source are previously added at the time of a hydrothermal synthesis, and the resulting mixture is subjected to the hydrothermal reaction in an aqueous medium. In this case, it is preferred that a crystallization modifier such as an organic amine, above all, tetrapropyl-ammonium compound is added to the aqueous medium.

The usable silica sources include water glass, silica sol, silica gel and silica powder, and in particular, water glass and silica sol can be preferably used. The usable alumina sources include sodium aluminate, aluminum nitrate, aluminum sulfate, alumina sol and alumina, but sodium aluminate, aluminum nitrate and aluminum sulfate are preferable.

Further, the usable boron sources include boron, ammonium borate, potassium borate, sodium borate, calcium borate and boron oxide.

On the other hand, examples of the alkali metal sources include sodium oxide, sodium aluminate, sodium hydroxide, potassium hydroxide, sodium chloride and potassium chloride in water glass.

Further, the alkaline earth metal sources include organic salts such as acetates and propionates of alkaline earth metals, and inorganic salts such as chlorides and nitrates thereof. In this connection, examples of the alkaline earth metals include magnesium, calcium, strontium and barium, and in particular, calcium and strontium are preferable, and secondarily magnesium is preferable. Barium is liable to require a high temperature to display catalytic activity. Concrete examples of the alkaline earth metal sources include magnesium acetate, magnesium chloride, magnesium nitrate, calcium acetate, calcium chloride, calcium nitrate, strontium acetate, strontium chloride, strontium nitrate, barium acetate, barium chloride and barium nitrate, and they can be used alone or in combinations thereof.

Concrete examples of the crystallization modifiers include tetra-n-propylammonium bromide, tetra-n-propylammonium chloride, tetra-n-propylammonium iodide, a mixture of tri-n-propylamine and n-propyl bromide and tetrapropylammonium hydroxide, and tetra-n-propylammonium bromide is particularly preferable.

Components of the reaction mixtures which will be subjected to the hydrothermal reaction are blended in the following ratios:

$SiO_2/Al_2O_3$ (molar ratio): 10 to 3,000, preferably 40 to 1,000

$SiO_2/B_2O_3$ (molar ratio): 1 to 1,000, preferably 1 to 100

$OH^-/SiO_2$ (except a hydroxyl ion from an organic base) (molar ratio): 0.02 to 10, preferably 0.05 to 0.5

$H_2O/SiO_2$ (molar ratio): 1 to 2,000, preferably 10 to 500 tetrapropylammonium compound/$SiO_2$ (molar ratio): 0.01 to 3, preferably 0.02 to 0.4 alkaline eath metal/Al (atomic ratio): 0.03 to 300 referably 0.4 to 8

In order to prepare the mixture satisfying the above mentioned composition conditions, these components are mixed within the respective limited ranges, and when needed, an acid such as sulfuric acid, hydrochloric acid or nitric acid, or a hydroxide of an alkali metal is added thereto so as to adjust the pH of the system to a suitable level of 11 or less.

The thus obtained mixture is then subjected to the hydrothermal reaction under atmospheric pressure or an elevated pressure at 80° to 250° C., preferably 150° to 180° C. for about 1 to 200 hours, preferably 5 to 50 hours usually under heating and with stirring.

The reaction product is separated by filtration or centrifugal means and is washed with water in order to remove excessive ionic materials, followed by drying and calcining.

The thus obtained crystalline aluminoborosilicate containing the alkaline earth metal has the following composition in which the respective components are represented by molar ratios of oxides:

$$aM^1_2O \cdot bM^2O \cdot Al_2O_3 \cdot B_2O_3 \cdot cSiO_2 \cdot nH_2O \quad (I)$$

wherein $M^1$ is an alkali metal and/or a hydrogen atom, $M^2$ is an alkaline earth metal, a is a value of 0 to 2, b is a value of 0.1 to 100, c is a value of 12 to 3,000, and n is a value of 0 to 30.

This crystalline aluminoborosilicate has, for example, X-ray diffraction patterns shown in the following Table 1:

TABLE 1

| Lattice Spacing d (Å) | Relative Strength |
|---|---|
| 11.15 ± 0.15 | high |
| 10.01 ± 0.15 | medium |
| 7.42 ± 0.10 | low |
| 6.70 ± 0.10 | " |
| 6.35 ± 0.10 | " |
| 5.97 ± 0.10 | " |
| 5.67 ± 0.10 | " |
| 5.56 ± 0.10 | " |
| 5.34 ± 0.10 | " |
| 5.00 ± 0.10 | " |
| 4.59 ± 0.10 | " |
| 4.34 ± 0.10 | " |
| 4.24 ± 0.10 | " |
| 3.99 ± 0.10 | " |
| 3.84 ± 0.07 | high |
| 3.81 ± 0.07 | medium |
| 3.74 ± 0.07 | " |
| 3.70 ± 0.07 | " |
| 3.65 ± 0.07 | low |
| 3.45 ± 0.05 | " |
| 3.42 ± 0.05 | " |
| 3.30 ± 0.05 | " |
| 3.24 ± 0.05 | " |
| 3.04 ± 0.05 | " |
| 2.97 ± 0.05 | " |
| 2.01 ± 0.02 | " |
| 1.99 ± 0.02 | " |

Irradiation: Cu—Kα; Wave Length 1.5418 Å

The values in the above item "relative strength" have been relatively decided regarding a strength of 11.15±0.15 Å as 100%, as follows:

"high"=70 to 100%
"medium"=40 to 70%
"low"=0 to 40%

This alkaline earth metal-containing aluminoborosilicate is similar to a known zeolite having a pore diameter of 5 to 6 Å in point of the X-ray diffraction patterns, but the former has a higher $SiO_2/Al_2O_3$ molar ratio and alkaline earth metal/Al atomic ratio than the latter, and the former can also be distinguished from the latter by catalytic activity. Further, the manufacturing method of this alkaline earth metal-containing aluminoborosilicate is characterized by adding boron and a salt of the alkaline earth metal to raw materials in preparing a crystal, and this point is different from a conventional manufacturing process. In addition, the thus obtained product of the present invention is also distinct from the conventional one in catalytic performance.

In this way, the crystalline aluminoborosilicate containing the alkaline earth metal can be obtained, but it contains oxides of an alkali metal and an alkaline earth metal. And this crystalline aluminoborosilicate can be converted into a proton ($H^+$)-substituted hydrogen type crystalline aluminoborosilicate in a usual way, for example, by carrying out an ion exchange by the use of an inorganic acid such as hydrochloric acid, sulfuric acid or nitric acid, or an organic acid such as formic acid or acetic acid, or alternatively by carrying out ion exchange by the use of an ammonium compound, followed by calcining. In this case, all or a part of the alkali metal is easily replaced with the proton ($H^+$), but the alkaline earth metal is only partially replaced with the proton ($H^+$).

The known aluminosilicate modified with the alkaline earth metal is the hydrogen type or alkali metal type aluminosilicate into which the alkaline earth metal ion is introduced by the ion exchange process, and in this case, the introduced alkaline earth metal ion can be converted into the hydrogen type again by the ion exchange process. Such an aluminosilicate can be distinguished from the aluminoborosilicate used in the method of the present invention. In other words, at least a part of the alkaline earth metal in the aluminoborosilicate used in the method of the present invention is linked more tightly than in the known alkaline earth metal-containing aluminosilicate.

The zeolite comprising this aluminoborosilicate, when being in a dried, calcined or H-ion exchanged state, is modified with an alkaline earth metal compound which will be mentioned hereinafter. Examples of such alkaline earth metal compounds include salts, oxides and hydroxides of various alkaline earth metals. The usable salts of the alkaline earth metals include various inorganic and organic salts of the alkaline earth metals, but in particular, carboxylates as acetates, carbonates and nitrates are preferable, and phosphates and borates can also be used. With regard to carboxylates such as acetates, for example, magnesium acetate takes the form of MgO, when calcined in air at 500° to 600° C., but the other acetates take the form of carbonates, when calcined. Therefore, the respective acetates of Ca, Si and Ba can be considered to be precursors of the corresponding carbonates.

The modification is carried out by bringing the alkaline earth metal-containing aluminoborosilicate into contact with the alkali earth metal compound in a solution, and evaporating the solution to dryness (impregnation method), or alternatively by filtering or centrifugally separating the solution (separation method). As a solvent used in the solution modification, any one is suitable, in so far as it can dissolve the salt of the alkaline earth metal, but an aqueous solution is particularly suitable. Further, it is also acceptable that the salt, oxide or hydroxide of the metal is merely mixed with the alkaline earth metal-containing aluminoborosilicate in the state of solid (mixing method). In the case of this mixing method, a particle diameter of the alkaline earth metal-containing aluminoborosilicate is 10 micrometers or less, preferably 5 micrometers or less, particularly preferably 1 micrometer or less, but particles having a diameter of 20 micrometers or more may be mixedly present therein. Further, a particle diameter of the alkaline earth metal compound to be mixed therewith is 20 micrometers or less, preferably 10 micrometers or less, particularly preferably 5 micrometers or less, but particles having a diameter of 30 micrometers or more may be mixedly present therein. When the particle diameter of the alkaline earth metal-containing aluminoborosilicate and the alkaline earth metal compound which will be mixed with each other is excessively large, a functional effect of the present invention will diminish or will be substantially lost. Mixing these materials may be carried out in the state of their solid powders or in the state of a slurry in a suitable dispersant. The dispersant for the carbonate or hydroxide suitably is water. The catalyst modified with the alkaline earth metal compound may be used directly without any additional treatment, or alternatively it may be used after calcined in air or a flowing $N_2$ gas.

In the catalyst obtained by modifying the alkaline earth metal-containing aluminoborosilicate, an amount of the alkaline earth metal incorporated for the modification is at least 0.25% by weight in terms of the metal, preferably 1 to 20% by weight in the cases of magnesium, calcium and strontium, and preferably 1 to 35% by weight in the case of barium. Since the zeolite containing an amine or ammonium can be converted into the hydrogen type only by calcining it, it is possible that the dried article is directly modified with the alkaline earth metal and is then calcined.

In the method of the present invention, the above mentioned catalyst can be directly used without any additional treatment, or alternatively it can be used, after being mixed with a suitable carrier such as clay, kaolin, alumina, silica or silica/alumina and then molded.

Next, reference will be made in detail to an operation and conditions of the method regarding the present invention by which the lower olefins are prepared from methanol and/or dimethyl ether by the use of the thus obtained catalyst.

As a conversion reaction of methanol and/or dimethyl ether, any reaction system is acceptable, in so far as it permits feeding the material in the state of a gas and bringing it into contact with the solid catalyst sufficiently. Examples of such conversion systems include a static bed reaction system, a fluid bed reaction system and a moving bed reaction system.

The reaction can be carried out under conditions in extensive ranges. For example, a reaction temperature is from 300° to 650° C., a weight hourly space velocity is from 1 to 10 $hr^{-1}$, and a total pressure is from 0.1 to 100 atm, preferably from 0.5 to 10 atm. The starting material can be diluted with water vapor or an inert gas such as nitrogen or argon and then fed onto the catalyst.

In the method of the present invention, the flow of a product is composed of water vapor, hydrocarbons and the unreacted material, and by suitable setting reaction conditions, a proportion of lower olefins such as ethylene and propylene can be increased in the hydrocarbons. The hydrocarbon products can be separated from water vapor and purified in a known manner.

In the manufacturing method of the lower olefins according to the present invention, methanol and dimethyl ether both are starting materials, and therefore in calculating a selectivity, the dimethyl ether produced from methanol should be regarded as the unreacted material.

The reaction for manufacturing the lower olefins from methanol and/or dimethyl ether according to the present invention is an exothermic reaction, and thus a temperature in a reaction system rises spontaneously, with the result that any problem is not present from the standpoint of energy consumption in the case that the reaction is carried out at an elevated temperature. A temperature control in this reaction system can be rather easily carried out, and since a reaction rate is accelerated, a small-scale reactor is enough advantageously. However, when a material of the reactor is, for example, stainless steel, it will tend to bring about some troubles to employ as high a temperature as 650° C. or more, and it can also be considered that at a high temperature of 650° C. or more, a catalytic crystal is apt to be broken owing to water vapor present in the reaction system. Therefore, an upper limit of the reaction temperature which can be employed in practice should be limited to a level of 650° C. or so.

It is to be noted that the catalyst prepared by modifying the alkaline earth metal-containing aluminoborosilicate with the alkaline earth metal which is employed in the method of the present invention has about 10 times as long a life as that of the known alkaline earth metal-modified zeolite catalyst and the previously suggested alkaline earth metal-containing aluminoborosilicate catalyst, and produces less amounts of B. T. X.

In the catalyst prepared by modifying the alkaline earth metal-containing aluminoborosilicate with the alkaline earth metal regarding the present invention, boron ions, similarly to aluminum ions, are replaced with a part of silicon atoms which constitute the main skeleton component of the zeolite.

EXAMPLES

Now, the present invention will be described in detail in accordance with examples, but the latter do not intend to limit the scope of the present invention.

Preparation 1

In 137 g of water were dissolved 8.11 g of tetra-n-propylammonium bromide, 2.28 g of aluminum nitrate nonahydrate, 3.77 g of boric acid, 2.68 g of calcium acetate and 4.96 g of sodium hydroxide in turn in this order, and 120 g of water glass (30 to 31% of $SiO_2$ and 0.37 to 0.46% of $Na_2O$; coloidal silica; Cataloid SI-30; Shokubai Kasei Co., Ltd.) was added thereto, followed by enough stirring in order to obtain an aqueous gel mixture. In this case, molar ratios of the respective materials were $SiO_2/Al_2O_3=200$, $SiO_2/B_2O_3=20$, $OH^-/SiO_2=0.2$, $H_2O/SiO_2=20$, tetra-n-propylammonium bromide/$SiO_2=0.05$ and $CaO/SiO_2=0.025$, and a Ca/Al atomic ratio was 0.57.

Next, this aqueous gel mixture was placed in a 2 liter autoclave, and a hydrothermal treatment was then carried out with stirring at 500 rpm under a self pressure at 160° C. for 16 hours. The reaction product was separated into a solid component and a solution portion by means of a centrifugal separator, and the solid component was then washed with water sufficiently, followed by drying at 120° C. for about 7 hours.

Next, the dried material was treated at 500° C. for about 5 hours in air, and 0.6N hydrochloric acid was mixed with the thus calcined Na type zeolite in a proportion of 13 ml of the former with respect to 1 g of the latter, and stirring was then carried out at room temperature for 24 hours. Afterward, the zeolite was washed with water sufficiently at room temperature and was then dried at 120° C. Next, calcination was carried out at 500° C. for about 3 hours in air in order to convert the zeolite into a hydrogen type, thereby obtaining an H type calcium-containing aluminoborosilicate. The obtained zeolite was composed of fine crystals each having a size of about 0.4 to 0.9 micrometer. With regard to this H type zeolite, its BET specific surface and the analytical results by a fluorescent X-ray method are set forth in Table 2. In addition, an X-ray deffraction pattern of the Na type zeolite is shown in FIG. 1.

Preparation 2

The same procedure as in Preparation 1 was repeated with the exception that there were used 7.82 g of tetra-n-propylammonium bromide, 2.28 g of aluminum nitrate nonahydrate, 0.47 g of boric acid, 1.34 g of calcium acetate and 1.71 g of sodium hydroxide, 170 g of water and 50 g of water glass (coloidal silica; Cataloid SI-30; Shokubai Kasel Co., Ltd.) and that a hydrothermal treatment was carried out in a 300 ml autoclave, in order to obtain an Na type zeolite. In this case, molar ratios of the respective materials were $SiO_2/Al$-

$_2O_3=100$, $SiO_2/B_2O_3=80$, $OH^-/SiO_2=0.1$, $H_2O/SiO_2=39$, tetra-n-propylammonium bromide/$SiO_2=0.1$ and $CaO/SiO_2=0.025$, and a Ca/Al atomic ratio was 0.79.

An X-ray diffraction pattern of the thus obtained Na type zeolite was substantially similar to that of FIG. 1, and crystals of the zeolite had as small a size as 0.4 to 1 micrometer.

A 5% aqueous ammonium chloride solution was mixed with this calcined Na type zeolite in a proportion of 13 ml of the former with respect to 1 g of the latter, and stirring was then carried out at room temperature for 1 hour. Afterward, the zeolite was washed with water sufficiently at room temperature, was dried at 120° C., and was then calcined at 500° C. for about 3 hours in order to convert it into a hydrogen type, thereby obtaining an H type calcium-containing aluminoborosilicate. With regard to this H type zeolite, its BET specific surface and the analytical results by a fluoroescent X-ray method are set forth in Table 2.

Next, this H type zeolite was subjected to a heat treatment at 600° C. for 45 hours in air, further treated at room temperature for 24 hours by the use of 0.6N hydrochloric acid, washed with water, dried, and then calcined at 500° C. for 3 hours.

Preparation 3

The same procedure as in Preparation 1 was repeated with the exception that there were used 7.82 g of tetra-n-propylammonium bromide, 2.28 g of aluminum nitrate nonahydrate, 1.88 g of boric acid, 1.34 g of calcium acetate and 2.99 g of sodium hydroxide, 170 g of water and 60 g of water glass (colloidal silica; Cataloid SI-30; Shokubai Kasei Co., Ltd.) and that a hydrothermal treatment was carried out under atmospheric pressure at 100° C. for 168 hours in a 500 ml quartz vessel instead of the autoclave, in order to obtain an Na type calcium-containing aluminoborosilicate. In this case, molar ratios of the respective materials were $SiO_2/Al_2O_3=100$, $SiO_2/B_2O_3=20$, $OH^-/SiO_2=0.2$, $H_2O/SiO_2=39$, tetra-n-propylammonium bromide/$SiO_2=0.1$ and $CaO/SiO_2=0.025$, and a Ca/Al atomic ratio was 0.58.

An X-ray diffraction pattern of the thus obtained Na type zeolite was substantially similar to that of FIG. 1, and crystals of the zeolite had as fine a size as 0.2 to 1 micrometer.

Next, in the same manner as in Preparation 2, the zeolite was converted into a hydrogen type and was then subjected to a heat treatment at 600° C. for 45 hours in air, followed by a treatment by the use of 0.6N hydrochloric acid.

With regard to two samples of this H type zeolite, their BET specific surfaces and the analytical results by a fluorescent X-ray method ar set forth in Table 2.

Preparation 4

In 90 g of water, 1.14 g of aluminum nitrate nonahydrate was dissolved to prepare a solution A, and 60 g of water glass (coloidal silica; Cacaloid SI-30; Shokubai Kasei Co., Ltd.) was dissolved in 40 g of water to prepare a solution B. The solution B was added to the solution A with vigorous stirring, and a solution of 1.26 g of sodium hydroxide in 20 g of water was added thereto. Further, another solution of 8.11 g of tetrapropylammonium bromide in 30 g of water was added thereto, and stirring was continued for about 10 minutes in order to obtain an aqueous gel mixture. In this case, a molar ratio of the materials were $SiO_2/Al_2O_3=200$, $OH^-/SiO_2=0.1$, $H_2O/SiO_2=40$, tetrapropylammonium bromide/$SiO_2=0.1$.

This aqueous gel mixture was placed in a 300 ml autoclave, and a hydrothermal treatment was carried out under a self pressure at 160° C. for 18 hours with stirring (500 rpm). A reaction product was separated into a solid component and a solution portion by means of a centrifugal separator, and the solid component was then washed with water sufficiently, followed by drying at 120° C. for about 5 hours. Next, the dried material was treated at 520° C. for about 5 hours in air, and 0.6N hydrochloric acid was mixed with the thus calcined Na type ZSM-5 in a proportion of 15 ml of the former with respect to 1 g of the latter, followed by stirring at room temperature for 24 hours. Afterward, the zeolite was washed with water sufficiently at room temperature and was then dried at 120° C. Next, calcination was carried out at 520° C. for 5 hours in air in order to convert the zeolite into a hydrogen type, thereby obtaining an H type ZSM-5. With regard to this H type ZSM-5, its BET specific surface and the analytical results by a fluorescent X-ray method are set forth in Table 2.

Five grams of the thus obtained H type ZSM-5 [$SiO_2/Al_2O_3=200$ (molar ratio)] were mixed with a solution of 3.14 g of $Ca(CH_3COO)_2 \cdot H_2O$ in 10 ml of water. After retained at about 80° C. for 20 hours, the mixture was then evaporated to dryness at a temperature of 100° to 110° C. in a drying stove. Afterward, calcination was carried out at 200° C. for 2 hours and then 500° C. for 18 hours in air in order to obtain a calcium-modified ZSM-5 (Ca content=0.144 gram per gram of the catalyst).

Preparation 5

The H type calcium-containing aluminoborosilicate obtained in Preparation 1 was subjected to a heat treatment at 600° C. for 45 hours in air and a 0.6N hydrochloric acid treatment in the same manner as in Preparation 2. With regard to this treated H type zeolite, its BET specific surface and the analytical results by a fluorescent X-ray method are set forth in Table 2.

Next, 1 g of this treated H type zeolite was mixed, in a mortar, with 0.5 g of a material prepared by first calcining calcium acetate at 500° C. for 18 hours and then grinding it in the mortar, with both the materials being in a solid state, thereby obtaining a calcium-modified zeolite.

A content of the calcined calcium acetate material for the modification in the obtained zeolite catalyst was 33.3%. And a proportion of the calcium acetate material to the zeolite wsa 50%, and it is 13.3% in terms of the metal. Thus, total calcium content in the modified zeolite was about 13.7%.

According to observed results of this modified zeolite by means of an electron microscope, the calcined calcium acetate particles each having a size of 0.5 micrometer or less were uniformly dispersed and deposited among the zeolite particles each having a size of about 0.4 to about 0.9 micrometer.

Preparation 6

The H type zeolite obtained in Preparation 2 was mixed with the calcined calcium acetate material in the same manner as in Preparation 5 in order to prepare a calcium-modified zeolite. In this modified zeolite, the calicined calcium acetate material for the modification was contained in an amount of 13.3% in terms of the metal. Thus total calcium content in the modified zeolite was about 14.2 wt%.

Preparation 7

The H type zeolite obtained in Preparation 3 was mixed with the calcined calcium acetate material in the same manner as in Preparation 5 in order to prepare a calcium-modified zeolite. In this modified zeolite, the calcined calcium acetate material for the modification was contained in an amount of 13.3% in terms of the metal. Thus, total calcium content in the modified zeolite was about 13.9 wt%.

Preparation 8

A solution of 26.4 g of $Ca(CH_3COO)_2.H_2O$ in 50 ml of water was mixed with 30 g of the H type zeolite obtained in Preparation 1. After retained at about 80° C. for 16 hours, the resulting mixture was evaporated to dryness at a temperature of 100° to 110° C. in a drying stove. Afterward, calcination was carried out at 500° C. for 16 hours in air in order to prepare a calcium-modified calcium-containing zeolite. In this modified zeolite, calcium acetate was contained in an amount of 16.9% in terms of the metal.

Preparation 9

One gram of the H type zeolite obtained in Preparation 1 was mixed, in a mortar, with 0.25% g of a material prepared by first calcining strontium acetate at 500° C. for 18 hours and then grinding it in the mortar, with both the materials being in a solid state, thereby obtaining a strontium-modified calcium-containing zeolite. A content of the calcined strontium acetate material was 20% in the thus obtained zeolite. And a proportion of the strontium acetate material to the zeolite was 25%; and it is 11.9% in terms of the metal.

Preparation 10

One gram of the H type zeolite obtained in Preparation 1 was mixed, in a mortar, with 0.5 g of a material prepared by first calcining strontium acetate at 500° C. for 18 hours and then grinding it in the mortar, with both the materials being in a solid state, thereby obtaining a strontium-modified calcium-containing zeolite. A content of the calcined strontium acetate material in the obtained zeolite was 33.3%. And a proportion of the strontium acetate material to the zeolite was 50%, and it is 19.8% in terms of the metal.

According to observed results of this modified zeolite by means of an electron microscope, the calcined strontium acetate particles each having a size of 0.5 micrometer or less were uniformly dispersed and deposited among the zeolite particles each having a size of about 0.4 to about 0.9 micrometer.

Preparation 11

One gram of the H type zeolite obtained in Preparation 1 was mixed, in a mortar, with 0.75 g of a material prepared by first calcining strontium acetate at 500° C. for 18 hours and then grinding it in the mortar, with both the materials being in a solid state, thereby obtaining a strontium-modified calcium-containing zeolite.

A content of the calcined strontium acetate material in the thus obtained zeolite was 42.9%. And a proportion of the strontium acetate material to the zeolite was 75%, and it is 25.5% in terms of the metal.

Preparation 12

A solution of 0.15 g of $Sr(CH_3COO)_2.\frac{1}{2}H_2O$ in 6 ml of water was mixed with 4 g of the H type zeolite obtained in Preparation 1. After retained at about 80° C. for 2 hours, the resulting mixture was evaporated to dryness at a temperature of 100° to 110° C. in a drying stove.

Afterward, calcination was carried out at 500° C. for 16 hours in air in order to prepare a strontium-modified calcium-containing zeolite. In this modified zeolite, strontium acetate was contained in an amount of 1.5% in terms of the metal.

Preparation 13

One gram of the H type zeolite obtained in Preparation 1 was mixed, in a mortar, with 0.50 g of a material prepared by first calcining barium acetate at 500° C. for 18 hours and then grinding it in the mortar, with both the materials being in a solid state, thereby obtaining a barium-modified calcium-containing zeolite.

A content of the calcined barium acetate material in the obtained zeolite was 33.3%. And a proportion of the barium acetate material to the zeolite was 50%, and it is 23.2% in terms of the metal.

According to observed results of this modified zeolite by means of an electron microscope, the calcined barium acetate particles each having a size of 0.5 micrometer or less were uniformly dispersed and deposited among the zeolite particles each having a size of about 0.4 to about 0.9 micrometer.

TABLE 2

| Preparation No. | Specific Surface ($m^2/g$) | Found | | | | |
|---|---|---|---|---|---|---|
| | | $SiO_2/Al_2O_3$ (molar ratio) | B (wt %) | Ca (wt %) | Na (wt %) | Ca/Al (atom ratio) |
| Preparation 1 | 344.3 | 196.2 | 0.16 | 0.36 | trace | 0.57 |
| Preparation 2 | 306.7 | 104.4 | 0.17 | 0.88 | " | 0.79 |
| Preparation 3 | 325.3 | 113.3 | 0.14 | 0.64 | " | 0.58 |
| Preparation 3* | 328.3 | 113.7 | 0.08 | 0.56 | " | 0.52 |
| Preparation 4 | 364.1 | 196.5 | 0 | 0 | " | 0 |
| Preparation 5* | 349.5 | 197.2 | 0.06 | 0.35 | " | 0.55 |

Note: *After a heat treatment at 600° C. for 45 hours, a 0.6 N hydrochloric acid treatment was carried out.

EXAMPLES 1 TO 9 AND COMPARATIVE EXAMPLES 1 AND 2

Each catalytic powder obtained in Preparations 1, 2 and 5 to 13 was pressed into tablets at a pressure of 400 kg/cm$^2$, and these tablets were then ground uniformly into a powder each particle of which had a size of 12 to 24 meshes. A quarts reaction tube having an internal diameter of 10 mm was then charged with 1 cc of the above prepared powder. A liquid methanol was forwarded to a carbureter at a flow rate 4 ml/hr, and was then mixed herein with an argon gas delivered at a flow rate of 40 ml/min. The resulting mixed gas was led to the above reaction tube under substantially atmospheric pressure, and reaction was carried out at 600° C. Each product was analyzed by the use of a gas chromatograph.

In Comparative Examples 1 and 2, the catalysts made in Preparations 1 and 2 were employed, and in Examples 1 to 9, the catalysts made in Preparations 5 to 13 were employed. The obtained results are set forth in Table 3.

It can be understood from Table 3 that according to the method of the present invention, a high yield of ethylene plus propylene is provided even under severe conditions such as a reaction temperature of 600° C. and WHSV=6 hr$^{-1}$, and a high catalytic activity is maintained for a long period of time.

EXAMPLES 10 TO 14 AND COMPARATIVE EXAMPLE 3

The same procedure as in Example 1 was repeated with the exception that the catalytic powders made in Preparations 4, 5, 8, 10, 12 and 13 were used, an amount of each catalyst to be charged is 2 cc, and a reaction temperature was 550° C.

In Examples 10 to 14, the catalysts made in Preparations 5, 8, 10, 12 and 13 were employed, and in Comparative Example 3, the catalyst made in Preparation 4 was employed. The obtained results are set forth in Table 4.

It can be understood from Table 4 that according to the method of the present invention, when a reaction temperature and WHSV are changed into 550° C. and 3 hr$^{-1}$ respectively, a high yield of ethylene plus propylene is maintained for a long period of time.

TABLE 3

| No. | Reaction Time*1 (hr) | Methanol Conversion (%) | Effective Conversion*2 (%) | Selectivity*3 | | | | | | | |
|---|---|---|---|---|---|---|---|---|---|---|---|
| | | | | CO | $CO_2$ | $CH_4$ | $C_2H_4$ | $C_2H_6$ | $C_3H_6$ | $C_3H_8$ | $C_4H_8$ |
| Comparative Example 1 | 2 | 100.00 | 100.00 | 0.38 | 0.14 | 1.42 | 14.85 | 0.28 | 44.37 | 0.42 | 17.80 |
| | 10 | 100.00 | 100.00 | 0.85 | 0.16 | 4.83 | 11.42 | 0.36 | 37.92 | 0.32 | 15.54 |
| Comparative Example 2 | 2 | 100.00 | 100.00 | 0.41 | 0.13 | 1.39 | 19.98 | 0.39 | 46.45 | 0.67 | 18.25 |
| | 14 | 100.00 | 100.00 | 2.27 | 0.26 | 9.37 | 13.70 | 0.51 | 35.86 | 0.41 | 14.54 |
| Example 1 | 2 | 100.00 | 100.00 | 1.59 | 1.85 | 1.09 | 13.52 | 0.17 | 48.06 | 0.42 | 20.98 |
| | 111 | 99.62 | 99.52 | 0.80 | 1.00 | 1.27 | 7.84 | 0.15 | 42.14 | 0.27 | 20.62 |
| Example 2 | 2 | 100.00 | 100.00 | 1.89 | 2.20 | 1.24 | 17.37 | 0.00 | 47.85 | 0.57 | 20.17 |
| | 110 | 100.00 | 100.00 | 1.18 | 1.11 | 1.25 | 8.30 | 0.00 | 41.46 | 0.30 | 20.12 |
| Example 3 | 2 | 100.00 | 100.00 | 1.46 | 2.04 | 1.22 | 17.31 | 0.00 | 47.32 | 0.53 | 19.42 |
| | 76 | 100.00 | 100.00 | 1.48 | 1.56 | 2.72 | 8.46 | 0.21 | 41.15 | 0.34 | 20.07 |
| Example 4 | 2 | 100.00 | 100.00 | 1.63 | 1.95 | 0.68 | 12.52 | 0.15 | 49.01 | 0.25 | 22.13 |
| | 157 | 99.02 | 99.02 | 0.58 | 0.76 | 0.69 | 7.25 | 0.09 | 42.79 | 0.19 | 21.48 |
| Example 5 | 2 | 100.00 | 100.00 | 1.62 | 1.17 | 0.88 | 14.59 | 0.20 | 47.22 | 0.42 | 19.99 |
| | 62 | 99.98 | 99.98 | 1.94 | 1.18 | 2.46 | 9.40 | 0.21 | 40.25 | 0.27 | 19.19 |
| Example 6 | 2 | 100.00 | 100.00 | 1.90 | 1.38 | 0.93 | 13.28 | 0.18 | 48.52 | 0.39 | 20.90 |
| | 107 | 99.07 | 99.07 | 1.80 | 1.07 | 1.86 | 8.25 | 0.18 | 41.24 | 0.25 | 19.32 |
| Example 7 | 2 | 100.00 | 100.00 | 2.23 | 1.67 | 0.87 | 12.43 | 0.18 | 46.77 | 0.29 | 20.72 |
| | 101 | 99.76 | 99.76 | 1.91 | 1.17 | 1.03 | 8.09 | 0.13 | 41.64 | 0.16 | 19.63 |
| Example 8 | 2 | 100.00 | 100.00 | 0.55 | 0.16 | 0.88 | 11.19 | 0.16 | 44.87 | 0.24 | 19.52 |
| | 52 | 100.00 | 100.00 | 0.53 | 0.09 | 2.34 | 8.39 | 0.21 | 41.19 | 0.25 | 19.57 |
| Example 9 | 2 | 100.00 | 100.00 | 1.50 | 1.21 | 0.91 | 12.62 | 0.23 | 46.09 | 0.38 | 20.10 |
| | 38 | 100.00 | 100.00 | 0.64 | 0.38 | 2.21 | 9.34 | 0.22 | 39.95 | 0.32 | 18.41 |

| No. | Reaction Time*1 (hr) | Methanol Conversion (%) | Effective Conversion*2 (%) | Selectivity*3 | | | | | $C'_2 + C'_3$*5 | $C'_2 \sim C'_4$*6 |
|---|---|---|---|---|---|---|---|---|---|---|
| | | | | $C_4H_{10}$ | $C_5H_{10}$ | $C_5H_{12}$ | BTX | Others*4 | | |
| Comparative Example 1 | 2 | 100.00 | 100.00 | 0.86 | 1.06 | 0.20 | 5.08 | 13.14 | 59.22 | 77.02 |
| | 10 | 100.00 | 100.00 | 0.60 | 2.51 | 0.18 | 6.77 | 18.54 | 49.34 | 64.88 |
| Comparative Example 2 | 2 | 100.00 | 100.00 | 0.87 | 2.35 | 0.23 | 6.94 | 1.94 | 66.43 | 84.68 |
| | 14 | 100.00 | 100.00 | 0.57 | 3.10 | 0.21 | 12.05 | 7.15 | 49.56 | 64.10 |
| Example 1 | 2 | 100.00 | 100.00 | 0.88 | 6.25 | 0.32 | 0.39 | 4.48 | 61.58 | 82.56 |
| | 111 | 99.62 | 99.52 | 0.52 | 14.99 | 0.20 | 0.36 | 9.84 | 49.98 | 70.60 |
| Example 2 | 2 | 100.00 | 100.00 | 0.99 | 4.25 | 0.56 | 0.57 | 2.34 | 65.22 | 85.39 |
| | 110 | 100.00 | 100.00 | 0.60 | 12.99 | 0.33 | 0.41 | 11.96 | 49.76 | 69.88 |
| Example 3 | 2 | 100.00 | 100.00 | 0.82 | 1.67 | 0.47 | 0.76 | 6.96 | 64.63 | 84.05 |
| | 76 | 100.00 | 100.00 | 0.57 | 13.69 | 0.33 | 0.91 | 8.49 | 49.61 | 69.68 |
| Example 4 | 2 | 100.00 | 100.00 | 0.80 | 3.07 | 0.39 | 0.31 | 7.11 | 61.53 | 83.66 |
| | 157 | 99.02 | 99.02 | 0.48 | 7.82 | 0.20 | 0.40 | 17.27 | 50.04 | 71.52 |
| Example 5 | 2 | 100.00 | 100.00 | 0.79 | 4.50 | 0.41 | 0.62 | 7.59 | 61.81 | 81.80 |
| | 62 | 99.98 | 99.98 | 0.58 | 10.12 | 0.37 | 0.93 | 13.10 | 49.65 | 68.84 |
| Example 6 | 2 | 100.00 | 100.00 | 0.74 | 5.31 | 0.40 | 0.60 | 5.47 | 61.80 | 82.70 |
| | 107 | 99.07 | 99.07 | 0.55 | 12.66 | 0.35 | 0.91 | 11.56 | 49.49 | 68.81 |
| Example 7 | 2 | 100.00 | 100.00 | 0.75 | 5.82 | 0.42 | 0.45 | 7.40 | 59.20 | 79.92 |
| | 101 | 99.76 | 99.76 | 0.57 | 13.01 | 0.37 | 0.93 | 11.36 | 49.73 | 69.36 |
| Example 8 | 2 | 100.00 | 100.00 | 0.83 | 7.65 | 0.38 | 2.50 | 11.07 | 56.06 | 75.58 |
| | 52 | 100.00 | 100.00 | 0.59 | 9.76 | 0.36 | 3.35 | 13.37 | 49.58 | 69.15 |
| Example 9 | 2 | 100.00 | 100.00 | 0.66 | 7.97 | 0.37 | 0.66 | 7.30 | 58.71 | 78.81 |
| | 38 | 100.00 | 100.00 | 0.54 | 12.05 | 0.34 | 2.99 | 12.65 | 49.25 | 67.66 |

Notes:
*1 A period of time after the reaction temperature had reached 600° C.
*2 A conversion of a carbon base in the case that dimethyl ether was regarded as an unreacted material.
*3 A selectivity of a carbon base to all the products other than dimethyl ether which was regarded as an unreacted material.
*4 The other hydrocarbons are meant.
*5 A total amount of ethylene and propylene.
*6 A total amount of ethylene, propylene and butene.

TABLE 4

| No. | | Comparative Example 3 | | Example 10 | | | Example 11 | | Example 12 | | Example 13 | | Example 14 | |
|---|---|---|---|---|---|---|---|---|---|---|---|---|---|---|
| Temp. (°C) | 550 | 550 | 550 | 550 | 550 | 550 | 550 | 550 | 550 | 550 | 550 | 550 | 550 | 550 |
| Time*1 (hr) | 2 | 52 | 68 | 3 | 200 | 420 | 3 | 200 | 330 | 3 | 200 | 365 | 3 | 207 | 3 | 100 | 270 |
| Methanol Conversion (%) | 100.00 | 99.47 | 94.84 | 100.00 | 100.00 | 99.50 | 100.00 | 100.00 | 98.96 | 100.00 | 100.00 | 99.79 | 100.00 | 100.00 | 100.00 | 100.00 | 100.00 |
| Effective Conversion*2 (%) | 100.00 | 98.99 | 90.25 | 100.00 | 100.00 | 99.50 | 100.00 | 100.00 | 98.96 | 100.00 | 100.00 | 99.79 | 100.00 | 100.00 | 100.00 | 100.00 | 100.00 |
| Selectivity*3 (%) CO | 3.05 | 1.58 | 2.20 | 0.41 | 0.53 | 1.14 | 0.42 | 0.27 | 0.40 | 0.85 | 0.77 | 0.78 | 0.00 | 0.12 | 0.00 | 0.20 | 0.39 |
| CO₂ | 2.16 | 1.77 | 1.92 | 0.88 | 0.64 | 0.98 | 0.79 | 0.45 | 0.55 | 0.52 | 0.43 | 0.45 | 0.00 | 0.00 | 0.68 | 0.16 | 0.11 |
| CH₄ | 2.03 | 2.43 | 3.04 | 0.36 | 0.45 | 1.53 | 0.40 | 0.53 | 0.83 | 0.53 | 1.04 | 2.47 | 0.54 | 2.36 | 1.39 | 0.65 | 1.50 |
| C₂H₄ | 9.46 | 5.41 | 4.19 | 12.41 | 9.11 | 6.20 | 12.22 | 7.81 | 6.27 | 12.02 | 9.93 | 6.44 | 10.34 | 6.97 | 10.12 | 9.07 | 6.26 |
| C₂H₆ | 0.26 | 0.17 | 0.15 | 0.16 | 0.13 | 0.12 | 0.12 | 0.07 | 0.07 | 0.14 | 0.14 | 0.16 | 0.00 | 0.00 | 0.00 | 0.00 | 0.00 |
| C₃H₆ | 45.68 | 40.74 | 35.71 | 49.32 | 48.65 | 44.09 | 49.89 | 48.11 | 44.19 | 48.02 | 47.71 | 43.61 | 47.15 | 43.16 | 49.26 | 47.82 | 44.11 |
| C₃H₈ | 1.00 | 0.49 | 0.41 | 0.58 | 0.48 | 0.38 | 0.56 | 0.33 | 0.29 | 0.60 | 0.38 | 0.32 | 0.45 | 0.31 | 0.49 | 0.43 | 0.30 |
| C₄H₈ | 18.28 | 16.41 | 15.61 | 22.45 | 22.48 | 18.83 | 22.89 | 22.91 | 22.26 | 22.28 | 22.12 | 20.39 | 21.13 | 19.50 | 22.34 | 21.64 | 20.09 |
| C₄H₁₀ | 1.09 | 0.84 | 0.80 | 1.17 | 1.10 | 0.96 | 0.90 | 0.85 | 0.75 | 1.05 | 1.00 | 0.93 | 0.84 | 0.72 | 0.97 | 0.80 | 0.71 |
| C₅H₁₀ | 6.79 | 12.80 | 13.26 | 7.60 | 8.93 | 13.52 | 7.52 | 9.30 | 13.01 | 7.82 | 9.13 | 13.34 | 7.67 | 11.55 | 7.98 | 8.89 | 12.59 |
| C₅H₁₂ | 4.74 | 4.70 | 4.81 | 0.51 | 0.48 | 0.45 | 0.46 | 0.44 | 0.42 | 0.54 | 0.51 | 0.48 | 0.53 | 0.50 | 0.55 | 0.53 | 0.52 |
| BTX*4 | 1.77 | 0.98 | 0.84 | 0.57 | 0.49 | 0.67 | 0.34 | 0.27 | 0.45 | 0.44 | 0.36 | 0.53 | 2.53 | 3.32 | 0.24 | 1.35 | 2.03 |
| Others*5 | 3.50 | 11.67 | 17.04 | 3.58 | 6.53 | 11.13 | 3.49 | 8.66 | 10.51 | 5.19 | 6.48 | 10.10 | 8.83 | 11.40 | 5.98 | 8.45 | 11.39 |
| C₂⁼ + C₃⁼*6 | 55.14 | 46.15 | 39.90 | 61.73 | 57.76 | 50.29 | 62.11 | 55.92 | 50.46 | 60.04 | 57.64 | 50.05 | 57.49 | 50.13 | 59.38 | 56.89 | 50.37 |

Notes:
*1 A period of time after the reaction temperature had reached 550° C.
*2 A conversion of a carbon base in the case that dimethyl ether was regarded as an unreacted material.
*3 A selectivity of a carbon base to all the products other than dimethyl ether which was regarded as an unreacted material.
*4 A total amount of benzene, toluene and xylene.
*5 The other hydrocarbons.
*6 A total amount of ethylene and propylene.

Having described a specific embodiment of our bearing, it is believed obvious that modification and variation of our invention is within the scope of the present invention in view of the above teachings.

What is claimed is:

1. A method for preparing lower olefins which comprises bringing methanol and/or dimethyl ether into contact with an alkaline earth metal-containing zeolite in the gaseous phase, said method being characterized by performing the gaseous phase reaction in the presence of an alkaline earth metal-modified alkaline earth metal-containing zeolite catalyst; said alkaline earth metal-modified alkaline earth metal-containing zeolite catalyst being prepared by subjecting, to a hydrothermal treatment at a temperature of 80° to 250° C., a raw material which satisfies the composition conditions of an $SiO_2/Al_2O_3$ molar ratio=12 to 3,000, an $SiO_2/B_2O_3$ molar ratio=1 to 1,000, an $OH^-/SiO_2$ molar ratio=0.02 to 10, an $H_2O/SiO_2$ molar ratio=1 to 2,000, a tetrapropylammonium compound/$SiO_2$ molar ratio=0.01 to 3, and an alkaline earth metal/Al gram-atom ratio=0.03 to 300, in order to form an alkaline earth metal-containing aluminoborosilicate having a composition of

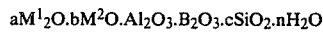

$aM^1_2O.bM^2O.Al_2O_3.B_2O_3.cSiO_2.nH_2O$ wherein $M^1$ is an alkali metal and/or a hydrogen atom, $M^2$ is an alkaline earth metal, a is a value of 0 to 2, b is a value of 0.1 to 100, c is a value of 12 to 3,000, and n is a value of 0 to 30; and modifying the thus formed alkaline earth metal-containing aluminoborosilicate with an alkaline earth metal compound in solid or solution form so that said alkaline earth metal in an amount of at least 0.25% by weight in terms of the metal may be mixed with or supported in said zeolite.

2. A method for preparing lower olefins according to claim 1 wherein said gaseous phase reaction of methanol and/or dimethyl ether contacting wityh said catalyst is carried out at a weight hourly space velocity of 0.1 to 20 hr$^{-1}$ at a reaction temperature of 300° to 650° C. under a total pressure of 0.1 to 100 atm.

3. A method for preparing lower olefins according to claim 2 wherein said weight hourly space velocity is within the range of 1 to 10 hr$^{-1}$.

4. A method for preparing lower olefins according to claim 2 wherein said total pressure is within the range of 0.5 to 10 atm.

5. A method for preparing lower olefins according to claim 2 wherein said temperature is within the range of 450° to 600° C.

6. A method for preparing lower olefins according to claim 1 wherein said alkaline earth metal-modified alkaline earth metal-containing zeolite is an alkaline earth metal-modified calcium-containing zeolite.

7. A method for preparing lower olefins according to claim 1 wherein said alkaline earth metal-modified alkaline earth metal-containing zeolite is an alkaline earth metal-modified strontium-containing zeolite.

8. A method for preparing lower olefins according to claim 1 wherein said alkaline earth metal-modified alkaline earth metal-containing zeolite is an alkaline earth metal-modified barium-containing zeolite.

9. A method for preparing lower olefins according to claim 1 wherein said alkaline earth metal-modified alkaline earth metal-containing zeolite is an alkaline earth metal-modified magnesium-containing zeolite.

* * * * *